(12) United States Patent
Zerafati

(10) Patent No.: US 9,120,912 B2
(45) Date of Patent: Sep. 1, 2015

(54) IRRADIATED FLUOROPOLYMER ARTICLES HAVING LOW LEACHABLE FLUORIDE IONS

(75) Inventor: Saeid Zerafati, Villanova, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 14/118,981

(22) PCT Filed: May 23, 2012

(86) PCT No.: PCT/US2012/039050
§ 371 (c)(1),
(2), (4) Date: Nov. 20, 2013

(87) PCT Pub. No.: WO2012/162341
PCT Pub. Date: Nov. 29, 2012

(65) Prior Publication Data
US 2014/0148528 A1    May 29, 2014

Related U.S. Application Data

(60) Provisional application No. 61/489,826, filed on May 25, 2011.

(51) Int. Cl.
| | | |
|---|---|---|
| C08J 3/28 | (2006.01) | |
| C08F 2/46 | (2006.01) | |
| C08G 61/04 | (2006.01) | |
| C08K 3/22 | (2006.01) | |
| C08J 7/12 | (2006.01) | |
| C08K 5/00 | (2006.01) | |
| A61L 2/00 | (2006.01) | |
| A61L 2/08 | (2006.01) | |

(52) U.S. Cl.
CPC . *C08K 3/22* (2013.01); *C08J 7/123* (2013.01); *A61L 2/007* (2013.01); *A61L 2/0035* (2013.01); *A61L 2/0041* (2013.01); *A61L 2/081* (2013.01); *A61L 2/082* (2013.01); *A61L 2/087* (2013.01); *C08J 2300/102* (2013.01); *C08J 2327/16* (2013.01); *C08K 5/0058* (2013.01)

(58) Field of Classification Search
CPC ..... C08K 2/22; C08K 5/0058; C08J 2327/16; C08J 2300/102; C08J 71/23; C08L 27/16
USPC .......................................... 522/113, 1; 520/1
See application file for complete search history.

(56) References Cited

U.S. PATENT DOCUMENTS

| | | | |
|---|---|---|---|
| 3,962,373 A * | 6/1976 | Petrucelli | ...... 525/199 |
| 5,516,564 A | 5/1996 | Root et al. | |
| 7,012,122 B2 | 3/2006 | Kappler et al. | |
| 7,045,584 B2 | 5/2006 | Kappler et al. | |
| 7,192,646 B2 | 3/2007 | DiMascio et al. | |
| 7,241,817 B2 | 7/2007 | Bonnet et al. | |
| 7,514,480 B2 | 4/2009 | Mekhilef et al. | |
| 7,642,313 B2 | 1/2010 | Henry | |
| 2006/0243666 A1 | 11/2006 | Jenkins et al. | |
| 2006/0246008 A1 | 11/2006 | Jenkins et al. | |
| 2008/0139719 A1* | 6/2008 | Huang et al. | ...... 524/400 |
| 2008/0261050 A1 | 10/2008 | Hartzel et al. | |
| 2009/0155570 A1 | 6/2009 | Bonnet et al. | |
| 2009/0274912 A1* | 11/2009 | Bonnet | ...... 428/422 |

* cited by examiner

*Primary Examiner* — Ling Choi
*Assistant Examiner* — Jessica E Whiteley
(74) *Attorney, Agent, or Firm* — Thomas F. Roland

(57) ABSTRACT

The invention relates to fluoropolymer articles that have been irradiated with at least 5 Kilo Gray of radiation, where the resulting articles have low levels of leachable or extractable fluoride ion. The low fluoride ion migration from the irradiated article is due to the presence of low levels of metalic salts or oxides in the fluoropolymer composition. The invention is especially useful for fluoropolymer articles in which the fluorpolymer layer contacts a biological or pharmaceutical fluid, and that are subjected to sterilization by irradiation.

8 Claims, No Drawings

IRRADIATED FLUOROPOLYMER ARTICLES HAVING LOW LEACHABLE FLUORIDE IONS

This application claims benefit, under U.S.C. §119 or §365 of PCT Application. Number PCT/US2012/039050, filed May 23, 2012, and U.S. Provisional Application No. 61/489,826, filed May 25, 2011.

FIELD OF THE INVENTION

The invention relates to fluoropolymer articles that have been irradiated with at least 5 KiloGray of radiation, where the resulting articles have low levels of leachable or extractable fluoride ion. The low fluoride ion leaching from the irradiated article is related to the presence of low levels of metalic salts or oxides in the fluoropolymer composition. The invention is especially useful for fluoropolymer articles in which the fluoropolymer layer contacts a biological or pharmaceutical fluid, and where the article is subjected to sterilization by irradiation.

BACKGROUND OF THE INVENTION

Polymers based on vinylidene fluoride $CF_2=CH_2$ (VDF), such as, for example, PVDF (polyvinylidene fluoride) homopolymers and copolymer, are known to offer excellent mechanical stability properties, very great chemical inertness and good resistance to ageing. These qualities are useful in varied fields of application.

Additives are often added to fluorpolymers to improve their properties. For example: flame retardancy (U.S. Pat. No. 7,642,313), and whiteness after heat processing (adding sodium acetate as described in U.S. Pat. No. 7,045,584 and U.S. Pat. No. 7,012,122). White pigments, such a $TiO_2$ and ZnO have been added to improve the fluoropolymer whiteness, the whiteness can be diminished during heat processing.

U.S. Pat. No. 7,192,646 describes the use of 5 to 15 percent of acid acceptors in a fluroelastomer used in fuel hose. The acid acceptors include magnesium oxide, calcium hydroxide, litharge, dibasic lead phosphate, calcium oxide, and zinc oxide.

Irradiation of fluropolymers may be done for several reasons, such grafting of functional groups (such as the grafting of maleic anhydride onto a fluorpolymer as described in U.S. Pat. No. 7,241,817), to create branching and enhance properties (U.S. Pat. No. 7,514,480), and for sterilization of articles containing fluoropolymers (U.S. Pat. No. 5,516,564).

Many high-purity operations require clean, pure processing environments and containers. Polymers used in these applications must be extremely chemical resistant and capable of being easily sterilized. The high-purity polymers find use in applications including bags or other containers for high purity fluids, biological and biomedical media, as well as high purity chemicals and reagents. Fluoropolymer articles cannot always be easily sterilized in a steam autoclave, as they will melt together and become useless.

Fluoropolymers are known for their stability, and fluoride ion is very difficult to leach or extract from a fluoropolymer.

Unfortunately, fluoropolymers exposed to irradiation and other high energy radiation, can undergo scission of some polymer bonds, or can create carbon-carbon double bonds (which can cause decoloration), with the release of small amounts of fluoride ions and small fluoride-containing molecules. Other fluorinated compounds used in the polymerization of a fluoropolymer, residual monomer, and oligomers can also release fluoride ions and small fluroride-containing molecules. In addition to the fluorine ion, other leachable fluorine-containing small molecules include, but are not limited to: HF, fluorine-containing monomers and oligomers, and fluorinated surfactants. The fluoride ion is extremely reactive. While the concentration of extractable fluoride ion is low, there is a desire to reduce the level even further—especially in applications in which the fluoropolymer comes in contact with the human body, or in contact with fluids meant for contact with living organisms. In these cases leachable or extractable fluorine compounds need to be minimized to levels that are tolerable by the human body.

Surprisingly, it has now been found that the addition of small levels of some metal salts or oxides to fluoropolymers, substantially reduce the migration of the fluoride ion into the material contained in these vessels, especially after the fluoropolymer undergoes treatment by irradiation.

An added advantage of the invention is that the reduction of the fluoride ion concentration tends to reduce discoloration of the fluoropolymer, leading to a whiter article.

SUMMARY OF THE INVENTION

The invention relates to an irradiated fluoropolymer article comprising at least one fluoropolymer composition layer that will contact a fluid, wherein said fluoropolymer composition comprises at least one fluoropolymer and from 50 to 50,000 ppm of at least one metal salt or a metal oxide, and where said fluoropolymer composition has been exposed to at least 5 KGray of radiation.

The invention further relates to a sterile fluoropolymer article and wherein said fluoropolymer composition comprises from 50 to 50,000 ppm of at least one metal salt or a metal oxide, and the fluoropolymer has been exposed to at least 20 KGray of radiation; wherein said article, when formed into a 2 mil thick bag, and irradiated with 25-50 KGray of gamma radiation, and filled with a 80% strill water for injection/20% ethanol solution, with a surface to liquid volume ratio of 2.2 l/cm for 14 days at 40° C. results in less than 10 ppm of extracted fluoride ion.

The invention further relates to a process of forming a sterile fluoropolymer article involving the step of adding from 500 to 50,000 ppm of a metal salt or oxide to a fluoropolymer to form a fluoropolymer composition, followed by irradiation of the flouropolymer composition either before, or preferably after the fluoropolymer composition is formed into and article.

DETAILED DESCRIPTION OF THE INVENTION

The invention relates to a fluoropolymer composition containing at least one fluoropolymer and low levels of at least one metal salt or oxide. These compositions have been found to have very low leachable fluoride ions following irradiation.

Unless stated otherwise, all percentages are weight percent, and all molecular weights provided are weight average molecular weights. All references cited herein are incorporated by reference.

Fluoropolymer

The fluoropolymers useful in the invention are those containing at least 50 weight percent of one or more fluoromonomers, preferably at least 75 weight percent of fluoromonomers and more preferably from 80 to 100 weight percent of fluoromonomers. The term "fluoromonomer" as used according to the invention means a fluorinated and olefinically unsaturated monomer capable of undergoing free radical polymerization reaction. Suitable exemplary fluoromonomers for use according to the invention include, but are not limited to, vinylidene fluoride, vinyl fluoride, trifluoroethylene, tetrafluoroethylene (TFE), ethylene tetrafluoroethylene, hexafluoropropylene (HFP), 2,3,3,3-tetrafluoropropene, and their respective copolymers. Preferred fluoropolymers are polyvinylidene fluoride homopolymer (PVDF) or copolymers thereof, polytetrafluoroethylene homopolymer or copolymers thereof, polyethylene trifluoroethylene (ETFE), and chlorothrifluoroethylene (CTFE). Fluoro-terpolymers are also contemplated, including terpolymers such as those having tetrafluoroethylene, hexafluoropropene and vinylidene fluoride monomer units.

In one preferred embodiment, the fluoropolymer is a polyvinylidene fluoride. Polyvinylidene fluoride polymers of the invention include the homopolymer made by polymerizing vinylidene fluoride (VDF), and copolymers, terpolymers and higher polymers of vinylidene fluoride, (referred to herein as a group as "copolymers), where the vinylidene fluoride units comprise greater than 70 percent of the total weight of all the monomer units in the polymer, and more preferably, comprise greater than 75, more preferably greater than 80 weight percent of the total weight of the monomer units. Copolymers, terpolymers and higher polymers of vinylidene fluoride may be made by reacting vinylidene fluoride with one or more monomers from the group consisting of vinyl fluoride, trifluoroethene, tetrafluoroethene, one or more of partly or fully fluorinated alpha-olefins such as 3,3,3-trifluoro-1-propene, 1,2,3,3,3-pentafluoropropene, 3,3,3,4,4-pentafluoro-1-butene, and hexafluoropropene, 2,3,3,3-tetrafluoropropene (1234 yf), the partly fluorinated olefin hexafluoroisobutylene, perfluorinated vinyl ethers, such as perfluoromethyl vinyl ether, perfluoroethyl vinyl ether, perfluoro-n-propyl vinyl ether, and perfluoro-2-propoxypropyl vinyl ether, fluorinated dioxoles, such as perfluoro(1,3-dioxole) and perfluoro(2,2-dimethyl-1,3-dioxole), allylic, partly fluorinated allylic, or fluorinated allylic monomers, such as 2-hydroxyethyl allyl ether or 3-allyloxypropanediol, and ethene or propene.

Preferred copolymers include those comprising from about 71 to about 99 weight percent VDF, and correspondingly from about 1 to about 29 percent TFE; from about 71 to 99 weight percent VDF, and correspondingly from about 1 to 29 percent HFP, and from about 71 to 99 weight percent VDF, and correspondingly from about 1 to 29 weight percent chlorotrifluoroethylene (CTFE).

Most preferred PVDF copolymers include are those having 2 to 30 weight percent of HFP, such as KYNAR FLEX 2850, 2750 and 2500 resins (Arkema Inc.).

While the invention applies to all fluoropolymers, the invention will be illustrated herein in its relation to polyvinylidene fluoride. One of skill in the art can use teachings herein to apply this technology to other fluoropolymer compositions.

Metal Salt or Oxide

It has been found that the addition that the addition of low levels of metal salts or oxides into fluorpolymer composition can substantially reduce the level of fluorine ion migration following exposure of articles formed from the fluorpolymer composition to radiation. Very small levels of fluoride ions and the corresponding added cations leach out of polyvinylidene fluoride (PVDF) after exposure liquid media. Following exposure of the PVDF composition to radiation, the level of leachable fluoride ion increases substantially, while the levels of leached cations do not change appreciably. For example, when low levels of zinc oxide (ZnO) are added to a fluoropolymer composition, an article formed from this fluoropolymer composition and exposed to radiation is found to have dramatically decreased levels of leachable fluoride ion, with only a small increase in leachable cation. The amount of leached Zn cation is proportional to the amount of the addition of the ZnO to the PVDF.

There are several factors that affect the choice of the metal salts and oxides to be used in the invention. These include:

1) the surface to weight ratio of the salt or oxide. The materials with smaller particle sizes are generally more effective in reducing the leachable fluoride ion. However in some cases, as with zinc oxide, micro zinc oxide was found to be more effective than nano zinc oxide at reducing the level of leachable fluoride ion.

2) The metal atoms with a higher number of valence electrons are more efficient in reacting with the fluoride ions or fluorine-containing molecules.

3) The salts should be free flowing for handling and processing during extrusion. This also means that their particles would not stick to each other upon exposure to atmospheric moisture. This is important because, in some cases, primary particles are very fine but upon exposure to moisture they would stick to each other and their surface to weight ratio would substantially reduce. Moreover, water soluble salts tend to leach into the water based fluids easily.

4) Most importantly the salts should not be toxic to, and preferably very compatible with living organisms. If the fluoropolymer composition is used to form the surface of an article in contact with, or containing a fluid that will come in contact with, a biological system, the level of cations must be below levels that are toxic to the living organism. It is known that the leached ions (both anions and cations) could prevent cell growth or have other harmful effects.

The level of leached fluoride ion should be less than 10 ppm, preferably less than 5 ppm, more preferably less than 1 ppm, even more preferably less than 500 ppb, and most preferably less than 100 ppb following irradiation. It is noted that a level of sodium fluoride of about 1 ppm or less is added by many municipalities to the drinking water supply. This level of leachable ions is based on the leachable ions from a 2 mil thick PVDF bag radiated with 25-50 KGray, preferably 40-50 KGray of gamma radiation with surface to liquid volume ratio of 2.2 l/cm containing a mixture of 80% sterile water for injection (SWFI) and 20% ethanol stored for 14 days at 40° C.

While reducing the level of leachable fluoride ion, the level of leachable cations also needs to be minimized below toxic levels for those cations. Some anions and cations are known to be present in living organisms, and are required for cell metabolism. These include, with average normal concentrations in human serum: sodium (3200 ppm), calcium (100 ppm), potassium (170 ppm), magnesium (20 ppm) and zinc (1 ppm) cations, as well as sulfate, phosphate, chloride, carbonate, and bicarbonate anions.

The metal salts most useful in the invention are selected to include cations and anions compatible with living organisms—those having relatively high concentrations in in human serum. Preferred anions are magnesium, calcium, potassium, sodium and zinc, while preferred anions include, but are not limited to, phosphate, sulfate, chloride, oxide, acetate, and formate. Sodium salts are preferred since the human body can tolerate high levels of sodium ions—though sodium salts also tend to be more water soluble than many other salts—increasing the leachability and also absorbing large amounts of water. Calcium and potassium salts both have similar molecular weights, however, calcium has two valence electrons which means that it should be twice as efficient as potassium at similar weight additions. Magnesium has the advantage of being almost 40% lighter than sodium and calcium and also has two electron valences however, the concentration of this ion in the blood is almost ⅕ of calcium. Zinc is also a preferred cation, having two valence electrons, though it is almost 60% heavier than calcium.

In addition to sulfate, phosphate, chloride, carbonate, and bicarbonate anions, nitrate anions are also useful. Oxides are a preferred anion since they are not toxic to the human body and are light. Acetate, formate, sterate, oxylate and other organic anions are also preferred, since they contain only carbon, hydrogen and oxygen and are generally bio-compatible. Zinc oxide is especially preferred since it is a stable, non-hygroscopic, and has a low water solubility. Useful salts and oxide of the invention include, but are not limited to:

Sodium Salts:

Sodium acetate, sodium acetate trihydrate, sodium aluminate, sodium aluminum chloride, sodium ammonium phosphate, sodium ammonium sulfate, sodium metaborate, sodium carbonate, sodium chlorate, sodium chlorite, sodium hypochlorite, sodium cinnamate, sodium citrate, sodium enanthate, sodium ethyl sulfate, sodium fluoroaluminate, sodium fluoroborate, sodium fluoride, sodium fluoroacetate, sodium fluorosulfonate, sodium formaldehyde-sulfoxylate, sodium formate, sodium mono glutamate, sodium glycerophosphate hydrate, sodium hydroxide, sodium magnesium sulfate, sodium magnesium tartrate, sodium methoxide, sodium methyl sulfate, sodium molybdate, sodium nitrate, sodium oleate, sodium oxalate, sodium peroxide, sodium palmitate, sodium pentobarbital, sodium phenoxide, sodium hypophosphates, sodium hypophosphate, sodium propionate, sodium salicylate, sodium selenite, sodium stannate, sodium silicates, sodium succinate, sodium stearate, sodium sulfate, sodium sulfide, sodium sulfite, sodium tungstate, sodium lactate, sodium nitrite, sodium phosphates, sodium phosphites, sodium tartrate, sodium lithium sulfate, sodium chloride, sodium benzoate, sodium ammonium tartrate, sodium alumina trisilicaate.

Calcium Salts:

Calcium acetate, calcium acetate dihydrate, calcium acetate monohydrate, calcium butyrate, calcium carbonate, calcium chlorate, calcium chloride, calcium chloride aluminate, calcium hypochlorite, calcium cinnimate, calcium citrate, calcium fluorosilicate, calcium formate, calcium gluconate, calcium hydroxide, calcium maleate, calcium maleate, calcium nitrate, calcium oxide, calcium phenol sulfonate, calcium phenoxide, calcium phosphates, calcium phosphite, calcium propionate, calcium salicylate, calcium sulfide, calcium sulfate, calcium stearate, calcium tungstate, calcium borate, calcium chlorite, calcium fumerate, calcium isobuterate, calcium lactate, calcium laurate, calcium linoleate, calcium oleate, calcium oxalate, calcium magnesium carbonate, calcium silicates, calcium nitrites, calcium succinate, calcium tartrate.

Magnesium Salts:

Magnesium acetate, magnesium acetate dihydrate, magnesium acetate monohydrate, magnesium butyrate, magnesium carbonate, magnesium chlorate, magnesium chloride, magnesium chloride aluminate, magnesium hypochlorite, magnesium cinnimate, magnesium citrate, magnesium fluorosilicate, magnesium formate, magnesium gluconate, magnesium hydroxide, magnesium maleate, magnesium maleate, magnesium nitrate, magnesium oxide, magnesium phenol sulfonate, magnesium phenoxide, magnesium phosphates, magnesium phosphite, magnesium propionate, magnesium salicylate, magnesium sulfide, magnesium sulfate, magnesium stearate, magnesium tungstate, magnesium borate, magnesium chlorite, magnesium fumerate, magnesium isobuterate, magnesium lactate, magnesium laurate, magnesium linoleate, magnesium oleate, magnesium oxalate, magnesium magnesium carbonate, magnesium silicates, magnesium nitrites, magnesium succinate, magnesium tartrate.

Potassium Salts:

Potassium acetate, potassium aluminate, potassium aluminosilicate, potassium ammonium tartrate, potassium benzoate, potassium borate, potassium boroxylate, potassium chlorate, potassium chloride, potassium carbonate, potassium magnesium sulfate, potassium citrate, potassium ethyl sulfate, potassium fluoroborate, potassium formate, potassium fluoride, potassium hydroxide, potassium lactate, potassium magnesium chloride, potassium magnesium selenate, potassium magnesium sulfate, potassium magnesium chloride, potassium methyl sulfate, potassium molybdate, potassium naphthalene disulfonate, potassium nitrate, potassium oleate, potassium oxalate, potassium oxide, potassium phosphates, potassium phthalate, potassium propionate, potassium propyl sulfate, potassium salicylate, potassium santoninate, potassium silicates, potassium tungstate, potassium sodium carbonate, potassium sodium sulfate, potassium sodium tartrate, potassium sorbate, potassium stannate, potassium stearate, potassium succinate, potassium sulfate, potassium sulfides, potassium tartrates, potassium tungstate, potassium xanthate, potassium ammonium aluminum sulfate, potassium magnesium chloride, potassium magnesium sulfate, potassium carbonate, potassium laurate, potassium malate, potassium methionate, potassium nitrite Zinc Salts:

Zinc acetate, zinc borate, zinc benzoate, zinc butyrate, zinc chlorate, zinc chloride, zinc citrate, zinc fluoride, zinc fluorosilicate, zinc formaldehyde sulfoxylate, zinc formate, zinc lactate, zinc laurate, zinc nitrate, zinc oleate, zinc oxalate, zinc oxide, zinc phosphates, zinc selenate, zinc sulfate, zinc sulfide, zinc tartrate, zinc valerate, zinc sulfite, zinc picrate, zinc hydroxide, zinc hypophosphite.

The level of metal salts added to the PVDF ranges from 50 to 50,000 ppm, preferably 100 to 10,000 ppm, and more preferably 500 to 5,000 ppm. The lower limit represents the effective level of salt needed to provide a significant decrease in the level of leachable fluoride ion, and other small fluorine-containing molecules, following radiation. The upper limit is open-ended, providing a reduction in leachable fluoride ion, however the excess cations may negatively effect other properties of the fluoropolymer composition.

Blending

The fluoropolymer composition of the invention is formed by blending the fluoropolymer with one or more metal salts or oxides. The blending can occur in any known manner. Generally the addition of the salt or oxide to the fluoropolymer will occur after polymerization and following any water-washing—especially for water soluble salts. However, it is within the scope of the invention that the metal salt or oxide could be added into the polymer latex at any point. The polymer latex and a salt or oxide solution/suspension could be co-spray dried to form the fluoropolymer composition. The metal salt could be added as the sole coagulant, or as a mixture with other coagulants in the coagulation stage of the process. The dry fluoropolymer powder could be dry blended with the metal salt or oxide, or the flurorpolymer and metal salt or oxide could even be added separately into a processing unit (such as an extruder) and be melt-blended just prior to pelletization or forming into a final article.

In addition to the fluoropolymer and metal salts or oxides of the invention, the polymer composition could also contain one or more typical additives including, but not limited to, pigments, dyes, fillers, surfactants, flame retardants, antioxidants, heat stabilizers, and other polymers miscible with PVDF, at low levels, generally below 5 wt percent in total, and preferably lower for high-purity applications.

The fluoropolymer composition of the invention is formed into articles by known means, such as by extrusion or co-extrusion, coating, injection molding, roto-molding, powder coating, fluidized bed coating and blow molding. The fluoropolymer composition of the invention is on the side of the article that will be in contact with a fluid—generally the inside surface for a tube, container, bag or vessel; though it could also be on both sides of an article such as a catheter that contacts fluids on both sides. An implant would have the fluoropolymer on the outside of the implant. The article can be a mono-layer or a multi-layer article. The fluoropolymer layer of the article is at least 1 mil in thickness. Fluoropolymer articles of the invention include, but are not limited to: containers (including for foods, milk, water, media, blood, solutions for intervenous delivery (IV) and pharmaceuticals), fittings, filters, tubing, bags, capillary tubes, pipettes, syringes, vessels, disposable reactors or reactor liners, connectors, stirrers, pipe, injection-molded articles, and packaging—including food packaging. In one embodiment a bag is formed by forming a multi-layer film that is then bonded along the edges to another film by heat sealing or radio frequency radiation. In another embodiment, the fluoropolymer composition is formed into a article by laser sintering, including an article such as a bone or joint replacement.

Irradiation is generally performed on the article after it is formed, though in some cases, as in polymer grafting, or irradiation for property improvement, the radiation can occur on the polymer powder prior to final fabrication into an article. In one embodiment, the article is exposed to radiation energy for the purpose of sterilization. By "sterile" or "sterilization", as used herein is meant that all forms of microbial life are destroyed. The exposure to radiation can be prior to contact of the fluoropolymer composition with a fluid—though it is anticipated that in some cases a bag containing an inner layer of the fluoropolymer composition can be formed, and filled with a fluid (such as a serum, saline solution, pharmaceutical or other fluid), and the irradiation of the bag and its contents could be done in a single step. Sterilization of the polymer composition of the invention can also include heat sterilization (autoclave). Heat energy for a time and intensity to achieve sterilization would generally result in an increase in fluoride ions—yet the composition of the invention would result in the levels of extractable fluoride ion to be below 10 ppm, preferably below 1 ppm, more preferably below 500 ppb, and most preferably below 100 ppb.

The form of irradiation used in the invention would include, but not be limited to, alpha, beta, and gamma radiation, laser energy, electron beam, x-rays, microwaves, and radio-frequency radiation—such as for welding of the fluropolymer. Electron beam (e-beam) and gamma radiation are especially preferred for sterilization. The level of radiation exposure would be greater than 5 KGray, preferably greater than 10 KGray, more preferably from 20-70 KGray for sterilization, and even more preferably 25-40 KGray. If the level of radiation is too low, sterilization will not occur, and the scission of the fluropolymer bonds is low. If the level of radiation is too high, the physical properties of the fluropolymer are effected.

The following examples further illustrate the best mode contemplated by the inventors for the practice of the invention and are to be construed as illustrative thereof and not in limitation thereof.

EXAMPLES

Example 1

Samples of KYNAR RX 801 HPC, a polyvinylidene fluoride copolymer from Arkema Inc. were compounded with 0, 500, 1,000, 2,000, and 3,000 ppm loadings of FDA grade AZO 66USP ZnO in an 18 mm Leistritz extruder. The resulting pellets were then gamma irradiation at 40-50 kGy and exposed to 40° C. for 14 days in a 20% EtOH/80% SWFI solution. The pellet test was used as an alternate method requiring less material and time than a method in which the polymer is formed into a mono-layer or multi-layer bag and filled with the fluid to test for extractables. Chromatography and ion-coupled plasma were used to characterize the anions and ions that leach into the solution. Following tables show the results:

TABLE 1

| | ICP Results—14 days at 40° C. | | | | | | | | | |
|---|---|---|---|---|---|---|---|---|---|---|
| | Al (ppm) | Ca (ppm) | Cu (ppm) | Fe (ppm) | Mg (ppm) | Mo (ppm) | Na (ppm) | Si (ppm) | Ti (ppm) | Zn (ppm) |
| Control 0 ppm | <0.03 | 0.05 | N.D. | 0.03 | <0.01 | 0.07 | <0.02 | <0.02 | N.D. | N.D |
| Control 500 ppm | <0.03 | <0.04 | N.D. | N.D | <0.01 | N.D | <0.02 | <0.02 | N.D. | 0.1 |
| Control 1000 ppm | <0.03 | 0.05 | N.D. | <0.02 | <0.01 | <0.07 | <0.02 | <0.02 | N.D. | 0.16 |
| Control 2000 ppm | <0.03 | <0.04 | N.D. | <0.02 | <0.01 | N.D. | <0.02 | <0.02 | N.D. | 0.27 |
| Control 3000 ppm | <0.03 | <0.04 | N.D. | <0.02 | <0.01 | <0.07 | <0.02 | <0.02 | <0.01. | 0.43 |
| Control Solution | <0.03 | <0.04 | N.D. | N.D. | <0.01 | N.D. | <0.02 | <0.02 | N.D. | N.D |
| Gamma 0 ppm | <0.03 | <0.04 | 0.06 | <0.02 | <0.01 | <0.07 | 0.07 | <0.02 | N.D. | N.D |
| Gamma 500 ppm | <0.03 | <0.04 | N.D. | N.D. | <0.01 | N.D | 0.08 | <0.02 | N.D. | 0.08 |
| Gamma 1000 ppm | <0.03 | <0.04 | N.D. | <0.02 | <0.01 | N.D. | 0.09 | <0.02 | N.D. | 0.14 |
| Gamma 2000 ppm | <0.03 | 0.08 | N.D. | <0.02 | <0.01 | N.D. | 0.01 | <0.02 | N.D. | 0.26 |

TABLE 1-continued

ICP Results—14 days at 40° C.

|  | Al (ppm) | Ca (ppm) | Cu (ppm) | Fe (ppm) | Mg (ppm) | Mo (ppm) | Na (ppm) | Si (ppm) | Ti (ppm) | Zn (ppm) |
|---|---|---|---|---|---|---|---|---|---|---|
| Gamma 3000 ppm | <0.03 | <0.04 | N.D. | <0.02 | <0.01 | N.D. | 0.08 | <0.02 | N.D. | 0.41 |
| Control Solution | <0.03 | <0.04 | N.D. | N.D. | <0.01 | N.D. | <0.02 | <0.02 | N.D. | N.D |

TABLE 2

ICP Results—14 days at 40° C.

|  | $F^-$ (ppm) | $HCOO^-$ (ppm) | $CH_3COO^-$ (ppm) | $Cl^-$ (ppm) | $NO_3^-$ (ppm) | $SO_4^{-2}$ (ppm) |
|---|---|---|---|---|---|---|
| Control 0 ppm | 0.31 | 0.36 | 0.17 | <0.1 | 0.17 | <0.1 |
| Control 500 ppm | 0.09 | 0.19 | 0.14 | <0.1 | 0.18 | <0.1 |
| Control 1000 ppm | 0.12 | 0.20 | 0.16 | <0.1 | 0.16 | <0.1 |
| Control 2000 ppm | 0.09 | <0.1 | 0.11 | <0.1 | 0.14 | <0.1 |
| Control 3000 ppm | 0.16 | <0.1 | 0.17 | <0.1 | 0.14 | <0.1 |
| Control Solution | 0.00 | <0.1 | 0.11 | <0.1 | 0.16 | <0.1 |
| Gamma 0 ppm | 18.50 | 0.86 | 0.17 | <0.1 | <0.1 | <0.1 |
| Gamma 500 ppm | 2.1 | 4.2 | 0.49 | <0.1 | 0.16 | <0.1 |
| Gamma 1000 ppm | 1.60 | 3.55 | 0.42 | <0.1 | 0.16 | <0.1 |
| Gamma 2000 ppm | 1.20 | 2.95 | 0.38 | <0.1 | 0.16 | <0.1 |
| Gamma 3000 ppm | 0.88 | 2.60 | 0.36 | <0.1 | 0.16 | <0.1 |
| Control Solution | 0.00 | ,0.1 | 0.11 | <0.1 | 0.02 | <0.1 |

As can be seen from the above results, addition of only 500 ppm of ZnO reduced the amount of leached fluoride ion from 0.31 ppm to 0.09 ppm before radiation and from 18.5 ppm to 2.1 ppm after radiation. Addition of the 500 ppm of ZnO resulted in the leaching of about 0.1 ppm of zinc cation. Radiation does not seem to have a major effect on the amount of leached zinc ion however, additional amounts of ZnO increases the level of leached zinc cation. The amount of leached fluoride ion appears to be a function of the weight of PVDF to the volume of the liquid. For a bag with 2 mil of PVDF on the inside, the amount of leachables are expected to be lower than the values reported above although the relative reduction or increase of the leached ions should remain the same.

What is claimed is:

1. An irradiated fluoropolymer article having low leachable fluoride ions comprising at least one fluoropolymer composition layer that will contact a fluid, wherein said fluoropolymer composition comprises a blend of at least one fluoropolymer selected from the group consisting of a polyvinylidene fluoride polymer having greater than 70 percent by weight of vinylidene fluoride monomer units, and polyethylene trifluoroethylene and from 50 to 50,000 ppm of at least one metal salt or a metal oxide, and wherein said fluoropolymer article has low leachable fluoride ions as determined by forming said fluoropolymer composition into a 2 mil thick bag, irradiating said bag with 25-50 KGray of gamma radiation, filling said bag with a 80% strill water for injection/20% ethanol solution, with a surface to liquid volume ratio of 2.2 l/cm for 14 days at 40° C., with the measured extracted fluoride ion being less than 10 ppm, and wherein said fluoropolymer composition contains less than 5 weight percent of additives selected from the group consisting of pigments, dyes, fillers, surfactants, flame retardants, antioxidants, heat stabilizers and polymers that are non-fluoropolymers.

2. The irradiated fluoropolymer article of claim 1, wherein fluoropolymer composition has been exposed to at least 20 KGray of radiation.

3. The irradiated article of claim 1, wherein the extracted fluoride ion is less than 500 ppb.

4. The irradiated fluoropolymer article of claim 1, wherein the extracted fluoride ion is less than 100 ppb.

5. The irradiated article of claim 1, wherein said radiation is selected from the group consisting of gamma radiation, alpha radiation, beta radiation, laser energy, and x-ray radiation.

6. The irradiated article of claim 1, wherein said article is a multi-layer article.

7. The irradiated article of claim 1, wherein said metal salt or metal oxide is formed from an anion selected from the group consisting of phosphate, sulfate, chloride, oxide, acetate, and formate, and a cation selected from the group consisting of magnesium, calcium, potassium, sodium and zinc.

8. The irradiated article of claim 1, wherein said fluoropolymer composition comprises from 500 ppm to 10,000 ppm of said metal salt or oxide.

* * * * *